United States Patent
Cline et al.

(10) Patent No.: US 6,247,368 B1
(45) Date of Patent: Jun. 19, 2001

(54) CMP WET APPLICATION WAFER SENSOR

(75) Inventors: Scott R. Cline, Enosburg Falls, VT (US); Willi O. Kalvaitis, West Chazy, NY (US); Richard J. Lebel, Williston, VT (US); Charles A. McKinney, Chazy, NY (US); Douglas P. Nadeau, Underhill, VT (US); Theodore G. van Kessel, Millbrook, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/225,149

(22) Filed: Jan. 4, 1999

(51) Int. Cl.[7] .......................... G01N 29/00; H02N 13/00
(52) U.S. Cl. ................................................ 73/629; 73/630
(58) Field of Search .................... 73/602, 629, 634, 73/432.1, 630, 597, 627; 367/93, 97, 105, 96; 437/247

(56) References Cited

U.S. PATENT DOCUMENTS

| | | | |
|---|---|---|---|
| 4,004,449 | 1/1977 | Gorey et al. ............................... 73/12 |
| 4,012,951 | 3/1977 | Kessler .................................. 73/67.6 |
| 4,344,160 | * 8/1982 | Gabriel et al. ........................... 367/96 |
| 5,177,711 | 1/1993 | Yamaguchi et al. ................... 367/105 |
| 5,222,329 | 6/1993 | Yu ..................................... 51/165.77 |
| 5,399,234 | 3/1995 | Yu et al. ................................ 156/636 |
| 5,540,098 | * 7/1996 | Ohsawa .................................. 73/629 |
| 5,600,068 | * 2/1997 | Kessler et al. ......................... 73/620 |
| 5,645,391 | * 7/1997 | Ohsawa et al. ...................... 414/416 |
| 5,668,452 | * 9/1997 | Villarreal et al. ............... 318/568.16 |
| 5,813,819 | * 9/1998 | Ohsawa et al. ...................... 414/416 |
| 5,922,136 | * 7/1999 | Huang ...................................... 134/2 |
| 5,948,986 | * 9/1999 | Brown .................................... 73/630 |

FOREIGN PATENT DOCUMENTS

| | | |
|---|---|---|
| 48-49155 | 7/1973 | (JP) . |
| 57-46383 | 8/1980 | (JP) . |
| 61-139834 | 1/1986 | (JP) . |
| 63-189310 | 8/1988 | (JP) . |
| 1-140727 | 6/1989 | (JP) . |
| 04147081 | 5/1992 | (JP) . |
| 06078399 | 3/1994 | (JP) . |
| 061774530 | 6/1994 | (JP) . |
| 06349793 | 12/1994 | (JP) . |
| 11265922 | 9/1999 | (JP) . |

* cited by examiner

Primary Examiner—Daniel S. Larkin
Assistant Examiner—Rose M. Miller
(74) Attorney, Agent, or Firm—DeLio & Peterson, LLC; Peter W. Peterson; Howard J. Walter

(57) ABSTRACT

A semiconductor post-polishing processing apparatus and method employing a non-optical wafer sensor for detecting the presence of a semiconductor wafer within the processing stations. The apparatus comprising a wet processing station, a wafer transport track, and the non-optical sensor. Preferably, the non-optical wafer sensor is a transducer, and most preferably, a piezo element, which emits and detects sound waves. The sound waves are reflected back to the emitter signaling the presence of a semiconductor wafer. The signal is sent to a receiver linked to a processor which is adapted to move a wafer holder situated at the end of the transport track to receive a wafer in the next available empty slot of the holder. The non-optical wafer sensor is impervious to slurry and CMP residue, film build-up, bubbles, wafer color/hue variations, and other wet environment problems.

13 Claims, 2 Drawing Sheets

CM P WET APPLICATION WAFER SENSOR

BACKGROUND OF THE INVENTION

1. Field of the Invention

This invention relates, in general, to the field of semiconductor manufacture. In particular, it relates to monitoring the presence of a semiconductor wafer during post chemical mechanical polishing (CMP) processing.

2. Description of Related Art

Fabrication of semiconductor integrated circuits (IC) is a complicated multi-step process for creating microscopic structures with various electrical properties to form a connected set of devices. As the level of integration of ICs increases, the devices become smaller and more densely packed, requiring more levels of photolithography and more processing steps. As more layers are built up on the silicon wafer, problems caused by surface non-planarity become increasingly severe and can impact yield and chip performance. During the fabrication process, it may become necessary to remove excess material in a process referred to as planarization.

A common technique used to planarize the surface of a silicon wafer is chemical mechanical polishing (CMP). CMP involves the use of a polishing pad affixed to a circular polishing table and a holder to hold the wafer face down against the rotating pad. A slurry containing abrasive and chemical additives are dispensed onto the polishing pad. The wafer and polishing pad rotate relative to each other. The rotating action along with the abrasive and chemical additives of the slurry results in a polishing action that removes material from the surface of the wafer. Protrusions on the surface erode more efficiently than recessed areas leading to a flattening or planarization of the wafer surface. Following CMP, the wafer must be cleaned of any CMP and slurry residue. Any residue remaining on the wafer can cause shorts in the IC devices.

The wafers are loaded into a wet processing station such as that shown in FIG. 1, and submerged in a water bath. The processing station contains a wafer transporter having a track which moves the wafers by means of a water jet pushing the wafers along the track. The wafers are then pushed into a cassette-like holder having horizontal slots for each wafer. The holder is motorized moving vertically to receive the wafer in the slot as it is being shot off the wafer transporter.

One or more sensors are used to track the presence of the wafers along the wafer transporter and prior to being inserted into the slots of the wafer holder.

Prior art methods employ sensors to track the presence of the wafers which utilize interruption of a signal path, for example, optical sensors using fiber optics. However, the optical sensors have proven unreliable due to film build-up, wafer color/hue variations, light refraction, sensing distance, bubble interference in water tracks, and other wet environment associated problems. These "false" sense events result in wafer breakage due to the inability of the sensor to correctly detect the presence of the wafer. The wafer breaks apart as the timing between the transport track and the holder are not in sync. Lost tool production in stopping the process adds to the already high cost of semiconductor wafer fabrication.

Bearing in mind the problems and deficiencies of the prior art, it is therefore an object of the present invention to provide a non-optical sensor which overcomes the problems of false sensing.

It is another object of the present invention to provide a sensor which is sustainable for use in a wet environment without regard to slurry contamination or CMP residue.

A further object of the invention is to provide a method of sensing a semiconductor wafer in a CMP processing station.

Still other objects and advantages of the invention will in part be obvious and will in part be apparent from the specification.

SUMMARY OF THE INVENTION

The above and other objects and advantages, which will be apparent to one of skill in the art, are achieved in the present invention which is directed to, in a first aspect, a semiconductor post-polishing processing apparatus comprising a wet processing station; a wafer transport track leading from the wet processing station; and a non-optical sensor for detecting the presence or position of semiconductor wafers within the station of the processing apparatus.

Preferably, the non-optical sensor of the semiconductor post-polishing processing apparatus emits and detects sound waves. More preferably, the non-optical sensor of the semiconductor post-polishing processing apparatus comprises a piezo element. The sound waves are emitted and reflected back to the sensor to determine the presence or position of semiconductor wafers within the station of the processing apparatus. Most preferably, the non-optical sensor of the semiconductor post-polishing processing apparatus emits sound waves in a frequency range of about 175 to 200 kHz, and most preferably at a frequency of about 190 kHz. Alternatively, the non-optical sensor of the semiconductor post-polishing processing apparatus may comprise a mechanical sensor attached to the wafer transport track.

In another aspect, the present invention relates to a post-planarization processing system for semiconductor wafers comprising at least one processing station; a transport system for transporting the wafers within the processing stations in a wet environment; a non-optical sensing means for sensing the presence of the wafers along the transporter; and an end station located at the end of the transport system comprising a holder having a plurality of horizontal slots for individual placement of the wafers adapted for placement of each wafer in a slot as they leave the transport system.

The sensing means comprises a transducer capable of emitting sound waves and a detector for detecting reflection of the sound waves when there is a wafer present on the transport system. Preferably, the transducer is a piezo element. The post-planarization processing system may further include a processor for producing a signal when the presence of a wafer is not detected by the sensing means.

In still yet another aspect, the present invention relates to a method of detecting the presence or position of a semiconductor wafer in a post-polishing apparatus comprising the steps of: providing a post-polishing apparatus having a wet environment; providing a semiconductor wafer situated in the post-polishing apparatus within the wet environment; emitting an acoustic wave; reflecting the acoustic wave to produce an electrical signal; processing the electrical signal resulting from the wave reflection; and comparing the electrical signal with a threshold signal to determine the presence and position of the semiconductor wafer.

Preferably, the emitter and detector of the post-polishing apparatus used in the method of detecting the presence or position of a semiconductor wafer is a piezo element operating at a frequency range of about 175 to 200 kHz, and most preferably at a frequency of about 190 kHz.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
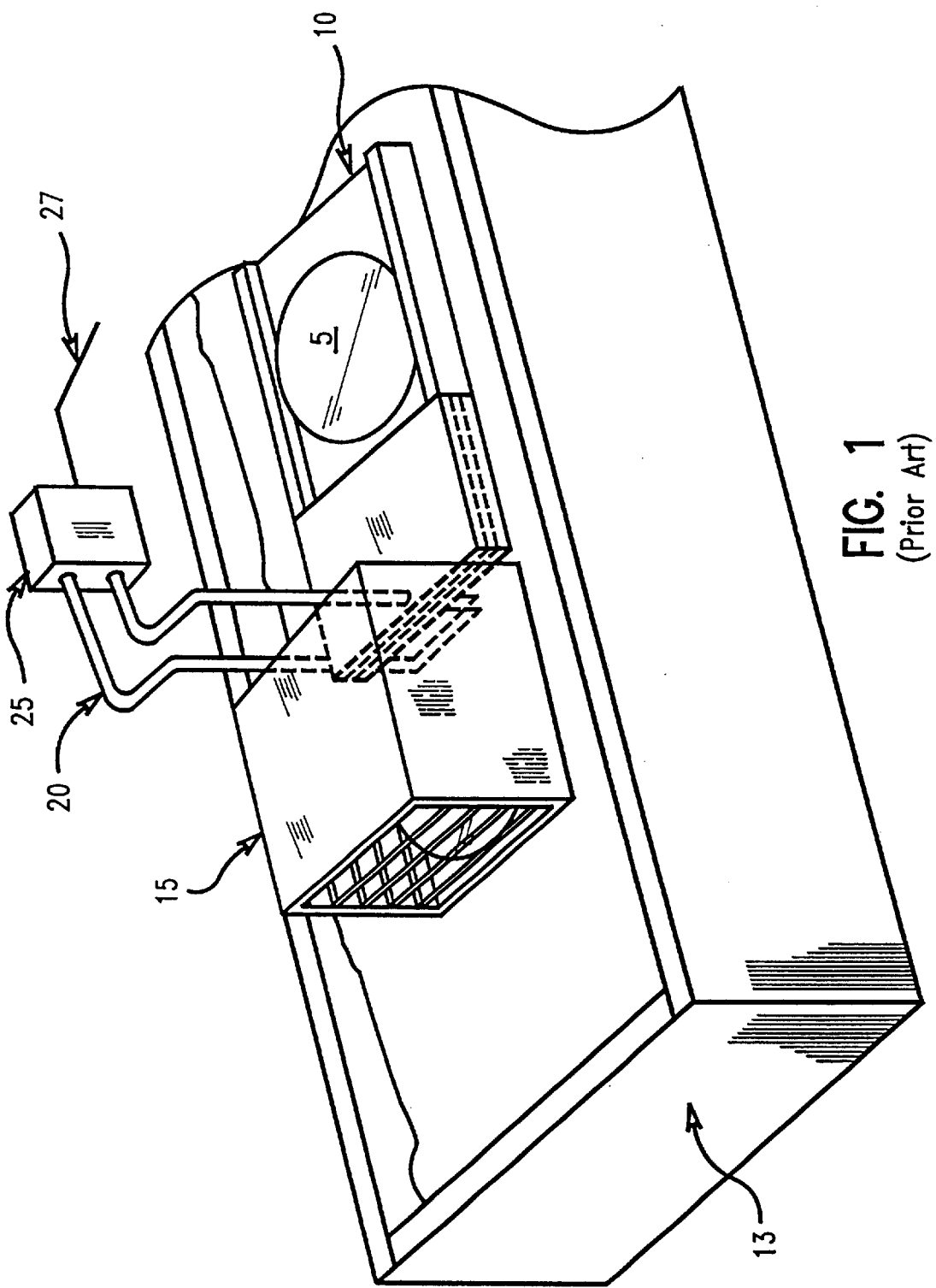
FIG. 1 is a schematic drawing showing a part of a post-CMP processing station having a wafer sensing means of the prior art.

In describing the preferred embodiment of the present invention, reference will be made herein to FIGS. 1–2 of the drawings in which like numerals refer to like features of the invention. Features of the invention are not necessarily shown to scale in the drawings.

FIG. 1 shows part of a post-CMP processing station having a wafer sensing means of the prior art. As a semiconductor wafer completes CMP, the wafers are loaded into a processing station to clean the wafers of any polishing residue and slurry. Further processing of a wafer with any remaining residue or slurry causes shorts in the IC. The wafers are loaded into a wet environment, usually a water bath 13. A transport track 10 is disposed slightly submerged below the surface of the water such that a wafer 5 floats in the water but is also supported by the track. The track is typically comprised of a plastic material.

High pressure water jets (not shown) push wafer 5 along track 10 through the water bath 13 of the processing station. As wafer 5 travels along the track through the processing station the water bath and the water jets substantially wash off slurry and CMP residue.

As the wafer reaches the end of transport track 10, a water jet shoots wafer 5 into a cassette-like holder 15. The wafer holder 15 has multiple horizontal slots which hold one wafer per slot. A portion of holder 15 is submerged under water but is adapted to move vertically allowing a wafer to be inserted into the next available empty slot.

To ensure that every slot of wafer holder 15 is filled, a wafer sensing means is placed near the end of transport track 10 to detect the presence of a wafer. Once a wafer is detected, a signal is sent to holder 15 to move up or down and receive the wafer in the next available slot.

When the wafer sensing means inaccurately detects the presence of a wafer this leads to partially filled holders and wafer breakage. The wafers are damaged when they are shot into a full slot, or in cases where the wafer is only partially in the slot as the holder moves to receive the next wafer. This results in higher costs of manufacturing due to down time in order to dislodge broken wafers and slows tool productivity at the next processing step when the wafer holders are only partially filled.

Prior art wafer sensing means, as shown in FIG. 1, are well known and generally comprise a wafer sensing means which send a continuous signal. Transmitter/receiver 25 sends a continuous signal such as a beam of light. When the light beam is interrupted, as in a fiber optics system referred to as numeral 20, the interruption signals the presence of a wafer 5. The output signal for a wafer present 27 is linked to a processor which then moves holder 15 to the next available empty slot for wafer 5.

There are many problems associated with the fiber optics sensing means 20 which interfere with wafer detection. Slurry particles and CMP residue present in the water bath tend to create a film over the sensor with time. There are difficulties encountered when the wafers are different colors depending on the composition of the layers on the wafer; some light may be refracted due to the reflection off the wafer. Other difficulties which interfere with sensing the wafer include bubble interference, inability to sense the distance, and other wet environment problems.

Figure 2:
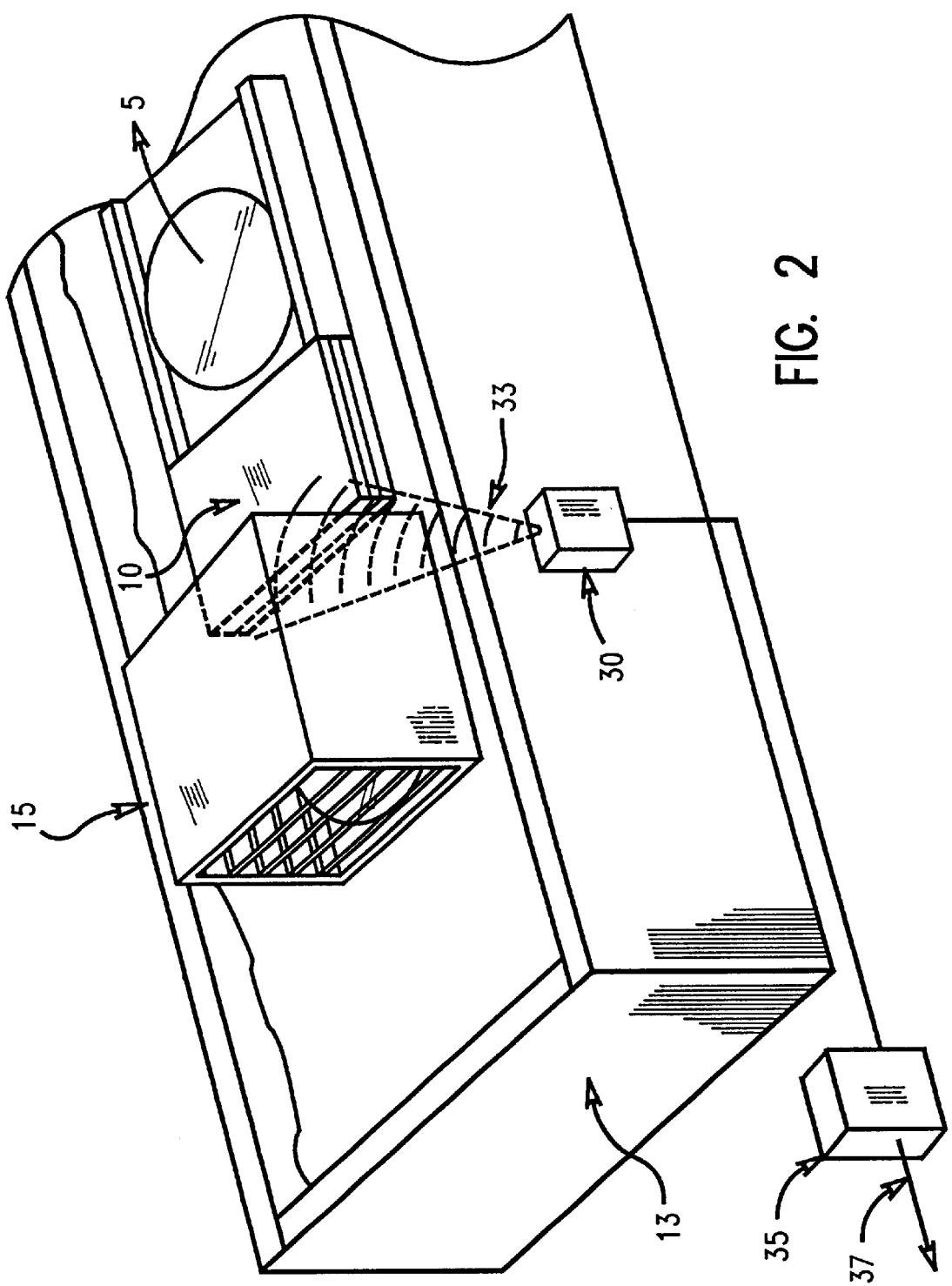
FIG. 2 is a schematic drawing showing a part of a post-CMP processing station having a wafer sensing means of the present invention.

In FIG. 2, the preferred embodiment of the present invention is shown. Again wafer 5 is transported along track 10 in a processing station having water bath 15. The wafer is moved along track 10 by high pressure water jets. This water bath and the water jets substantially remove any slurry and CMP residue from the surfaces of wafer 5. The wafer is cleaned and shot into wafer holder 15.

The non-optical wafer sensing means of the present invention does not have any of the wet environment problems associated with the prior art as discussed above. A preferred embodiment of the present invention comprises a transducer 30 which can be located at any point on the bottom of water bath 13 along the direction of track 10. Most preferably, the transducer is situated directly below the end of track 10. Transducer 30 emits and detects sound waves in the angular pattern referred to as numeral 33. The angular pattern 33 of the sound waves can be tailored for each application or different batches. Unexpectedly, the sound waves permeate the plastic material of track 10 allowing the presence of the wafer to be detected at different points as it moves along the track.

Transducer 30 is, preferably, a piezo element which is electrically excited in the aqueous environment of water bath 13 to emit sound waves. When a wafer is in proximity, the emitted wave is reflected back to the piezo element and detected by a receiver 35. A return signal 37 in excess of a threshold value is interpreted as "wafer present." This signal in turn is linked to a processor which is adapted to move the wafer holder for a wafer to be inserted into the next available empty slot.

Alternatively, another embodiment (not shown) of a non-optical sensor employed in the water bath of the post-CMP processing station may be a mechanical sensor. As a wafer passes along the track, the wafer hits a trigger sending a "wafer detected" signal to the wafer holder to move accordingly to the next available empty slot for insertion of the wafer.

The present invention achieves the objects recited above. The use of a non-optical wafer sensing means does not have the drawbacks of the systems of the prior art which send out a continuous signal such as a fiber optic system. The transducer used to emit and detect sound waves is not affected by water, bubbles, or wafer color/hue variations. Film build-up on the transducer does not prevent the transducer from emitting sound waves and detecting the presence of a wafer. The present invention significantly reduces the number of false positives which in turn reduces wafer breakage occurrences, and down time associated with wafer breakage and partially filled wafer holders.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A semiconductor post-polishing processing apparatus comprising:
   a wet processing station for processing semiconductor wafers in a wet environment;
   a wafer transport track leading from said wet processing station; and
   a non-optical acoustic sensor for detecting the presence of the semiconductor wafers within said station of said processing apparatus, the sensor detecting the presence of the semiconductor wafers by detecting sound waves propagated through the wet environment and reflected from the semiconductor wafers.

2. The semiconductor post-polishing processing apparatus according to claim 1, wherein said non-optical acoustic sensor comprises a piezo element.

3. The semiconductor post-polishing processing apparatus according to claim 1, wherein said sound waves are emitted by the acoustic sensor and reflected back to said sensor to determine the presence of the semiconductor wafers within said station of said processing apparatus.

4. The semiconductor post-polishing processing apparatus according to claim 3, wherein said non-optical acoustic sensor emits and detects sound waves in a frequency range of about 175 to 200 kHz.

5. The semiconductor post-polishing processing apparatus according to claim 4, wherein said non-optical acoustic sensor emits and detects sound waves in a frequency range of about 175 to 200kHz.

6. The semiconductor post-polishing processing apparatus according to claim 4, wherein said non-optical acoustic sensor emits and detects sound waves in a frequency range of about 190kHz.

7. The post-planarization processing system according to claim 6, wherein said sensing means comprises a transducer capable of emitting sound waves and a detector for detecting reflection of the sound waves when there is a wafer present on said transport system.

8. The post-planarization processing system according to claim 7, wherein said transducer is a piezo element.

9. The post-planarization processing system according to claim 6, further including a processor for producing a signal when the presence of a wafer is not detected by said sensing means.

10. A method of detecting the presence of a semiconductor wafer in a post-polishing apparatus comprising the steps of:
    providing a post-polishing apparatus having a wet environment;
    providing a semiconductor wafer situated in said post-polishing apparatus within the wet environment;
    emitting an acoustic wave to propagate through the wet environment;
    reflecting said acoustic wave from the semiconductor wafer in the wet environment to produce an electrical signal;
    processing said electrical signal resulting from the wave reflection; and
    comparing the electrical signal with a threshold signal to determine the presence of said semiconductor wafer.

11. The method according to claim 10, wherein said step of emitting an acoustic wave comprises emitting the acoustic wave to propagate through the wet environment with a piezo element.

12. The method according to claim 10, wherein said step of emitting an acoustic wave comprises emitting the acoustic wave to propagate through the wet environment with an emitter operating in a frequency range of about 175 to 200 kHz.

13. The method according to claim 10, wherein said step of emitting an acoustic wave comprises emitting the acoustic wave to propagate through the wet environment with an emitter operating in a frequency range of about 190 kHz.

* * * * *

UNITED STATES PATENT AND TRADEMARK OFFICE
CERTIFICATE OF CORRECTION

PATENT NO. : 6,247,368 B1
DATED : June 19, 2001
INVENTOR(S) : Scott R. Cline et al.

It is certified that error appears in the above-identified patent and that said Letters Patent is hereby corrected as shown below:

Column 5,
Delete duplicate claim 5.
Renumber claim 6 as claim 5.
Insert the following as new claim 6:
-- 6. A post-planarization processing system for semiconductor wafers comprising:
  at least one processing station;
  a transport system for transporting the wafers within said processing stations in a wet environment;
  a non-optical acoustic sensing means for sensing the presence of the wafers along said transport system, the acoustic sensing means detecting the presence of the wafers by detecting sound waves propagated through the wet environment and reflected from the wafers; and
  an end station located at the end of said transport system comprising:
  a holder having a plurality of horizontal slots for individual placement of the wafers adapted for placement of each wafer in a slot as they leave the transport system. --

Signed and Sealed this

Fifth Day of March, 2002

*Attest:*

*Attesting Officer*

JAMES E. ROGAN
*Director of the United States Patent and Trademark Office*